United States Patent
Laporte Uribe

(10) Patent No.: US 10,905,100 B2
(45) Date of Patent: Feb. 2, 2021

(54) METHOD AND APPARATUS FOR MONITORING NUTRITION, ESPECIALLY FERMENTATION IN A RUMEN OF A RUMINANT

(71) Applicant: GEA Farm Technologies GmbH, Bönen (DE)

(72) Inventor: Jose Alberto Laporte Uribe, Herdecke (DE)

(73) Assignee: GEA Farm Technologies GmbH, Bönen (DE)

( * ) Notice: Subject to any disclaimer, the term of this patent is extended or adjusted under 35 U.S.C. 154(b) by 249 days.

(21) Appl. No.: 15/117,120

(22) PCT Filed: Feb. 10, 2015

(86) PCT No.: PCT/EP2015/052696
§ 371 (c)(1),
(2) Date: Aug. 5, 2016

(87) PCT Pub. No.: WO2015/121220
PCT Pub. Date: Aug. 20, 2015

(65) Prior Publication Data
US 2016/0353710 A1 Dec. 8, 2016

(30) Foreign Application Priority Data

Feb. 14, 2014 (DE) .................. 10 2014 101 875
Dec. 12, 2014 (DE) .................. 10 2014 118 535

(51) Int. Cl.
*A01K 11/00* (2006.01)
*A01K 29/00* (2006.01)
(Continued)

(52) U.S. Cl.
CPC .............. *A01K 11/007* (2013.01); *A01K 1/12* (2013.01); *A01K 29/005* (2013.01);
(Continued)

(58) Field of Classification Search
CPC ..... A01K 11/007; A01K 29/00; A01K 29/005
See application file for complete search history.

(56) References Cited

U.S. PATENT DOCUMENTS

| | | | |
|---|---|---|---|
| 2003/0146834 A1* | 8/2003 | Stevens | A01J 5/007 340/531 |
| 2010/0183756 A1* | 7/2010 | Kobayashi | A23K 20/158 424/776 |
| 2013/0344005 A1* | 12/2013 | Le Jean | A61K 31/194 424/44 |

FOREIGN PATENT DOCUMENTS

| | | |
|---|---|---|
| GB | 2455700 A | 6/2009 |
| WO | 2012173502 A1 | 12/2012 |
| WO | 2013003892 A1 | 1/2013 |

OTHER PUBLICATIONS

Marden et al., "A New Device for Measuring Kinetics of Ruminal pH and Redox Potential in Dairy Cattle." J. Dairy Sci. 88:277-281, American Dairy Science Association, 2005.
(Continued)

*Primary Examiner* — Monica L Williams
(74) *Attorney, Agent, or Firm* — Smith Law Office; Jeffry W. Smith

(57) ABSTRACT

Methods and apparatus for monitoring nutrition, especially fermentation in a rumen of a ruminant, wherein a characteristic value of carbon dioxide inside the rumen and/or reticulum is determined.

16 Claims, 2 Drawing Sheets

(51) Int. Cl.
  *A61B 5/00* (2006.01)
  *A61B 5/01* (2006.01)
  *A61B 5/07* (2006.01)
  *A61B 5/145* (2006.01)
  *G01N 21/3504* (2014.01)
  *G01N 21/3577* (2014.01)
  *G01N 21/61* (2006.01)
  *G01N 33/00* (2006.01)
  *A01K 1/12* (2006.01)
  *H04B 7/24* (2006.01)

(52) U.S. Cl.
  CPC .............. *A61B 5/0031* (2013.01); *A61B 5/01* (2013.01); *A61B 5/073* (2013.01); *A61B 5/14539* (2013.01); *A61B 5/4238* (2013.01); *A61B 5/6861* (2013.01); *G01N 21/3504* (2013.01); *G01N 21/3577* (2013.01); *G01N 21/61* (2013.01); *G01N 33/004* (2013.01); *A61B 2503/40* (2013.01); *H04B 7/24* (2013.01)

(56) References Cited

OTHER PUBLICATIONS

International Search Report & Written Opinion, dated Apr. 8, 2015 for International Application No. PCT/EP2015/05269611, pages.
International Preliminary Report on Patentability, dated Aug. 16, 2016, for International Application No. PCT/EP2015/052696, 7 pages.
Emmanuel et al, "The Rumen Buffering System of Sheep Fed Pelleted Roughage-Concentrate Rations." British Journal of Nutrition, vol. 23, No. 4, pp. 805-811, 1969.
Jun. 19, 2019 Examination Report for Australian Application No. 2015217798, 6 pages.

* cited by examiner

METHOD AND APPARATUS FOR MONITORING NUTRITION, ESPECIALLY FERMENTATION IN A RUMEN OF A RUMINANT

FIELD AND BACKGROUND OF THE INVENTION

The subject matter of this invention relates to methods and apparatus for monitoring nutrition, especially fermentation in the rumen of a ruminant like a cow, a goat, a sheep and the like.

Ruminants are in many countries of the world used to produce milk and/or to produce meat. Both the milk and the meat production per ruminant have increased significantly over the last decades. Responsible for this rise is on one hand the genetic improvement of the ruminants e. g. by breeding and on the other hand a better understanding of the nutritional requirements of the cattle. In particular, in larger herds of dairy cattle the feed management of the herd frequently needs optimization. In particular, acidosis shall be avoided. Rumen acidosis is understood as an increase in acidity in the rumen described as a decline of the pH of the rumen content for a period of time which is enough to have physiological consequents on the animal affected by it. In that regards, metabolic and respiratory acidosis is understood as the increase in acidity of the blood and other tissues. In ruminants metabolic and respiratory acidosis is strongly coupled to the decline in rumen pH. Therefore, attempts were made to measure the rumen pH value in situ.

Prior art describes a bolus with an included pH meter and a temperature sensor e.g. in GB 2 455 700 A. This pH sensor functions electrochemically, i. e. it uses a pH electrode for measuring the pH value. Such a system is disadvantageous, as the used sensor drifts already after some weeks of use in the rumen.

SUMMARY OF THE INVENTION

Based on this it is an object of the present invention to provide a method and an apparatus for monitoring nutrition, especially fermentation in the rumen of ruminants. A further object is to monitor the onset of diseases associated to rumen acidosis.

The method according to the present invention for monitoring nutrition, especially fermentation in a rumen of a ruminant comprises the step of determination of a characteristic value of carbon dioxide inside the rumen and/or reticulum. The determination of the characteristic value can be made directly or indirectly by measuring a relevant chemical and/or a physical property.

The knowledge of the characteristic value can be used to improve the health of the ruminant, especially by regulating gas holdup and reduce foam formation within the rumen. That can be achieved by feeding management and ration formulation, especially the use of supplements, buffers, additives, antifoaming agents or other substances which may be a part of the feed.

The method according to the present invention for monitoring nutrition in the rumen of a ruminant comprises the step of measuring the concentration of dissolved carbon dioxide as a characteristic value. The concentration of dissolved carbon dioxide can be used to predict, prevent and control the onset of rumen acidosis, subacute rumen acidosis, metabolic and respiratory acidosis, bloat, abormasal dysplasia, low milk fat syndrome and other nutritional syndromes and diseases associated to gas holdup and/or foam formation in the gastrointestinal tract of ruminants.

The characteristic value, especially the concentration of dissolved carbon dioxide is preferably determined, especially measured at least at preterminable times inside the rumen.

The monitoring takes preferably place by a respective bolus. Preferably, the monitoring takes place in the rumen, reticulum and/or the ventral sac of the rumen. According to the method, the concentration of dissolved carbon dioxide is measured at least at predetermined times inside the rumen and the measured concentration of dissolved carbon dioxide is correlated with at least one respective pH value. The correlation of the concentration of the dissolved carbon dioxide with at least one respective pH value can for example be performed by using a predetermined algorithm to calculate the pH value from the respective concentration of dissolved carbon dioxide or by using a table with reference values for different couples of concentrations of dissolved carbon dioxide and respective pH values. The term "at least one respective pH value" can be understood in such a way that preferably one single pH value can be assigned to one specific concentration of dissolved carbon dioxide. Nevertheless, depending on the system used to measure the dissolved carbon dioxide concentration, it is possible that a value range, meaning a range limited by a minimum and a maximum pH value, is returned depending on the given concentration of dissolved carbon dioxide. This means that even in case of given pH ranges, it is always possible to provide e.g. a minimum pH value to have a clear indication of a condition in the rumen that might be dangerous for the animal with respect to a acidosis.

The rumen of ruminants has a so called biochemical buffer system which means that a chemical equilibrium between dissolved carbon dioxide, carbonic acid and hydrogen carbonate ion is given:

$$dCO_2 + H_2O \underset{k_{h2}}{\overset{k_{h1}}{\rightleftharpoons}} H_2CO_3 \underset{k_{a2}}{\overset{k_{a1}}{\rightleftharpoons}} HCO_3^- + H^+ \tag{1a}$$

The reaction equilibrium is determined by the $CO_2$ hydration constant $k_h$ and the equilibrium constant $k_a$ for the reaction between hydrogen carbonate and carbonic acid. Carbonic acid does not accumulate in solution but quickly dissociates into hydrogen and hydrogen carbonate. The subscripts 1 and 2 used in the above formula are used to differentiate between the forward 1 and reverse 2 reactions. For these the following relations are known:

$$k_h = \frac{k_{h1}}{k_{h2}} \tag{1b, 1c}$$

and $$k_a = \frac{k_{a1}}{k_{a2}}$$

The equilibrium between the dissolved carbon dioxide concentration and the hydrogen carbonate concentration is governed by the following equation:

$$k_{eq} = \frac{k_{h1} * k_{a1}}{k_{h2} * k_{a2}}, \tag{2a, 2b}$$

or, $$k_{eq} = \frac{[HCO_3^-] + [H^+]}{[dCO_2] + [H_2O]}$$

Applying a decadic logarithm to this equation leads to the following finding:

$$\log K_{eq} = \log H^+ + \log \frac{[HCO_3^-]}{[dCO_2]} \quad (3)$$

$$pH = -\log H^+,$$

and $$pK_a = -\log K_a$$

Consequently:

$$pH = pK_{eq} + \log \frac{[HCO_3^-]}{[dCO_2]} \quad (4)$$

This means that the pH can be determined if the concentrations of dissolved carbon dioxide, of hydrogen carbonate and the equilibrium constant $k_a$ are known.

It enhances the buffer capacity by providing carbon dioxide to or receiving carbon dioxide from the dissolved carbon dioxide following thermodynamic equilibrium. A determination of the carbon dioxide partial pressure in the above given equation allows the calculation of the concentration of dissolved carbon dioxide.

The relationship between the concentration of dissolved carbon dioxide, the concentration of the hydrogen carbonate ions and the pH value is given above. This can be solved for given hydrogen carbonate ion concentrations to allow to correlate the measured value of dissolved carbon dioxide with at least one pH value. The range in pH values can be due to a slight variation in the concentration of hydrogen carbonate ions.

The method according to the present invention allows to monitor the rumen pH value and/or the rumen dissolved carbon dioxide concentration. This allows to issue a warning if the pH value falls below a predetermined threshold, like e. g. a pH value below 6.1. At the same time preferably the measurement times are monitored as well, either in an apparatus within the rumen or by a transfer to the outside of the animal. This allows to monitor the time intervals in which specific acidic conditions are present as it was found that rumen acidosis has been divided according to the presentation of clinical signs into two: subclinical and clinical acidosis. There is an increase awareness that not only is necessary to reach certain threshold of rumen pH, but also the length of time below certain threshold is important. Although subclinical acidosis has been defined as an altered rumen environment where the rumen is below pH 5.8 for more than 12 hours per day, it has been suggested that the risk of developing subclinical acidosis increases if the rumen is under pH 5.8 for more than 5 hours per day, maybe because under those conditions the digestion of fiber and fermentation become altered.

Clinical rumen acidosis can be divided into acute and subacute. In general, values below pH 5.5 for more than 5 hours have been shown to produce clinical signs of subacute acidosis; whereas clinical acidosis is most of the time associated to values below pH 5.0, which are critical, even for shorter periods of time.

We were able to estimate the increase in dissolved carbon dioxide due to the decline in rumen pH for that broad physiological range (7 to 5, FIG. 2). In this way, the pH threshold described for optimal bacterial fermentation (below pH 6.6), decline in fiber digestion (below pH 5.8), subacute acidosis (below pH 5.5) and acidosis (below pH 5.0) can be traced to different $dCO_2$ concentrations 12 to 20, 60, 120 and 380 mM, respectively. Those values for dissolved carbon dioxide relate closely to changes in biological activity of bacteria responsible for fermentation in the rumen and physiological changes of the rumen epithelia associated the rumen acidosis. Hence, the idea is that dissolved carbon dioxide concentrations are the control mechanism for the onset of rumen acidosis rather than the associated decline in rumen pH.

Alternatively or in addition, the characteristic value is the pH value. The pH value can be measured directly be using a pH sensor or indirectly by measuring the dissolved carbon dioxide concentration as explained above.

It is preferred to monitor the concentration of dissolved carbon dioxide at discrete point of times, preferably in intervals of less than one minute. Nevertheless, it is possible to change this time interval, in particular based on predetermined circumstances, e. g. for some time after feeding. This can be triggered by an outside signal, e. g. from a communication unit combined with the feeding equipment or the like.

Furthermore, the gathered data can be used to generate information regarding the efficiency of fermentation in the rumen and the risk of nutritional diseases, including syndromes and diseases such as subclinical acidosis, acute acidosis, bloat, abomasal dysplasia, ketosis and others. This analysis can either be performed in an analysis unit in the apparatus or outside, after transmission via a first communication unit inside the rumen and a second communication unit being situated outside the animal By this, it is possible to generate specific warning signals for the farmer if specific criteria, like e. g. a pH of less than 5.8 for 5 hours per day or for 12 hours and more per day or concentrations of dissolved carbon dioxide greater than 60 mM for 5 hours.

According to an improvement of the method, the concentration of dissolved carbon dioxide is measured using an infrared sensor.

Infrared sensors, i. e. sensors being sensible for electromagnetic radiation in the infrared regime, in particular active infrared sensors sending out an infrared radiation through a sample and measuring the light after passing the sample at least once, possibly twice or more, by use of at least one respective mirror, allows a stable measurement of the dissolved carbon dioxide without drift of the measurement values. In particular, internal calibration standards to avoid a drift of the measurement values can be provided cumulatively. Preferred is a so called NDIR sensor, a non dispersive infrared sensor.

Such a sensor preferably comprises a source of infrared radiation, a sample, e. g. a filled body made from glass, through which the infrared radiation can pass and a respective infrared detector. Further preferred is the use of a wave length filter that only allows radiation of a specific wavelength regime to pass.

Preferably, the sensor comprises a measurement chamber into which the dissolved carbon dioxide can diffuse, e. g. through a membrane, preferably a polytetrafluorethylene (PTFE) membrane.

Such an NDIR sensor is easily adaptable to be used in the method and can be used with a low consumption of electric energy. This allows to provide a bolus for oral application to the animal staying permanently in the rumen of the respective animal Such sensors allow a bolus lifetime being longer than the usual life time of dairy or meat cattle and also small ruminants.

According to a further improvement at least one of the following data
  a) the measured concentration of dissolved carbon dioxide and
  b) the respective pH value
is transmitted wirelessly to a receiver outside the ruminant.

This can e. g. be performed using a RF (radio frequency) transmitter and receiver. This allows to collect data about a herd of ruminants automatically and centrally allowing the farmer to easily access the data of his herd. A respective equipment can e. g. be implemented to a parlor or a milking equipment as respective antennas allowing RF transmission.

The use and the transmission of the concentration of dissolved carbon dioxide allows the monitoring of these data, which can preferably be performed instead of the monitoring of the pH value in the rumen.

According to a further improvement the pH value is calculated based on a predetermined relationship between the concentration of the dissolved carbon dioxide and the pH value.

This relationship can e. g. be derived from the above given equation (4) using a biochemical model for the concentration profile of the hydrogen carbonate ions.

According to a further improvement the method includes a measurement of the temperature in the rumen.

This can further increase the quality of the data provided by the method according to the present invention as the temperature in the rumen influences the chemical equilibria being the basis of the above-given equations. Therefore, a further correlation with the temperature in the rumen during the measurement of the dissolved carbon dioxide is advantageous.

According to a further aspect of the invention an apparatus for monitoring nutrition, especially fermentation in the rumen of a ruminant is proposed, including at least the following units:
  a) at least one sensing unit for sensing a characteristic value of carbon dioxide in the rumen and/or reticulum; and
  b) at least one first communication unit for the wireless communication of data with a respective second communication unit outside the ruminant, wherein the apparatus is designed to be orally applied to the ruminant and to stay permanently in the rumen and/or reticulum.

Preferably, the apparatus comprises at least one sensing unit for sensing the concentration of dissolved carbon dioxide in the rumen. Alternatively or in addition the apparatus comprises at least one sensing unit for sensing the pH value as a characteristic value of carbon dioxide in the rumen and/or reticulum.

The apparatus is preferably designed as an indwelling probe (a bolus) having a shape and a size to allow to be orally applied to the animal and to be resistant to the chemical environment in the rumen. Preferably, the apparatus comprises a battery or an accumulator, in particular an accumulator that can be reloaded wirelessly. Alternatively, passive RFID devices can be used which receive the necessary electric energy wirelessly as well. Such a system is then preferably designed such that it is activated by the energy transfer to take measurements of the dissolved carbon dioxide in that instance.

The first communication unit in one embodiment in particular works as a transmission unit that is able to send data to a receiving unit (the second communication unit). Generally, the first communication unit preferably comprises an antenna and a respective RF (radio frequency) unit to allow transmission and receiving information to and from the second communication unit with a respective antenna outside the animal Preferable, the radio frequency transmission might ranges between 999 MHz to 1 MHz and between 999 kHz to 1 kHz, depending on damping effect of the rumen content and the optimal distance transmission between the bolus and the antenna or receiver.

Preferably, the apparatus further comprises a storage device in which data can be stored at least for some time. Such storage device comprises preferably a flash memory or the like. This storage device can be used to buffer measurement data if no communication with the second communication unit is temporarily possible, as e. g. the second communication device is installed in a milking parlor and/or in the feeding environment and the animal is currently outside.

The preferred source of electrical energy is a battery. Preferred is a battery that has an electrical capacity allowing the use of the apparatus more than a year, in particular more than three years to cover the usual life times of dairy cattle and beef animals.

If an accumulator is used as a source of electrical energy internal loading, means are preferred that convert small movements of the apparatus into electrical energy. These movements can e. g. be the peristaltic movements of the animal. Alternatively or in addition, means for loading the accumulator due to a conversion of movement energy to electrical energy can be used.

Preferably, the apparatus has a weight between 65 to 200 grams with a specific weight of more than 2.75 g/cm$^3$ [grams per cubic centimeter]. Preferably, the apparatus has a diameter of 20 to 26 mm [millimeters]. Preferably, for use with cattle, the apparatus has a length of 66 to 100 mm.

According to an improvement, the sensing unit includes at least one infrared sensor.

Infrared sensors for measuring the concentration of carbon dioxide have been proven to be reliable and are available as a lab on a chip to allow to be implemented in the apparatus according to the present invention. In particular useful is a NDIR infrared sensor as described above.

The use of an NDIR sensor is advantageous as these sensors have frequently a very low power consumption which reduces the strain on the energy provision system of the apparatus, preferably a respective battery. Preferably, a self calibrating NDIR sensor is used as the sensing unit.

The sensing unit comprises a measurement chamber which is exposed to rumen gases, preferably by using a membrane being permeable for the gases. Preferably, this is a membrane comprising polytetrafluorethylene (PTFE), sold e. g. under the brand Teflon. These membranes are permeable for carbon dioxide, i. e. allowing carbon dioxide to diffuse from the rumen and/or reticulum liquid into the measurement chamber but being reasonably corrosion resistant to allow the apparatus to stay in the rumen liquid and/or reticulum liquid. Preferably, the membrane is shaped such that the shape of the whole apparatus is smoothed, in particular in the edge regions to allow an easier oral application.

According to a further improvement the apparatus further comprises a temperature sensor for sensing the temperature in the rumen and/or reticulum liquid.

According to a further improvement the apparatus further comprises correlation means for correlating the value of the concentration of dissolved carbon dioxide with at least one pH value.

According to a further improvement the apparatus further comprises an encasement made at least in part from stainless steel.

This ensures a reasonable life time of the apparatus in the chemical environment of the rumen. Preferably the stainless steel encasement is covering at least the first communication unit, the sensing unit and a battery or accumulator. Preferably, the stainless steel encasement is combined with a glass surface to allow sending infrared light from the light source of the infrared light, preferably a respective light emitting diode, into a measuring chamber of the sensing unit.

According to a further improvement it is suggested for calibrating purposes to provide the sensing unit with a light source especially a LED of the same wavelength as the infrared sensor.

According to a further aspect of the present invention a milking parlor, comprising at least one second communication unit for wireless communication with a first communication unit in an apparatus according to present invention is proposed.

Other features which are considered as characteristic for the invention are set forth in the appended claims, noting that the features presented individually in the claims can be combined in any technologically meaningful way and give rise to additional embodiments of the invention.

We described the use of dissolved carbon dioxide ($dCO_2$) in the rumen of cattle to monitor and prevent nutritional diseases. In brief, the dissolved carbon dioxide ($dCO_2$) holdup, in the rumen liquor due to physicochemical changes and fast fermentation of nutrients might explain many of the nutritional diseases and syndromes that are endemic of dairy farming. As a matter of example:

Rumen Acidosis and SubAcute Rumen Acidosis (SARA): The dissolved carbon dioxide ($dCO_2$) accumulation due to physicochemical changes in the rumen liquor will trigger rumen acidosis by reducing bacterial activity, decline of feed intake and nutrient digestion, prolonged period of high dissolved carbon dioxide ($dCO_2$) concentrations will modify the acid-base balance of the rumen epithelia and increase in $CO_2$ diffusion into the bloodstream will results in the establishment of metabolic and respiratory acidosis in cattle.

Abomasal dysplasia: The outflow of gas saturated rumen liquor into the abomasum (true stomach) will mean that large amount $CO_2$ and $CH_4$ can be released in the abomasum after acid digestion, which will displace the abomasum to abnormal anatomical locations in the abdominal cavity, condition that has to be surgically corrected.

Bloat: The formation of stable foam in the rumen is a consequence and manifestation of the dissolved carbon dioxide ($dCO_2$) holdup due to physicochemical changes of the rumen liquor during fermentation. Foam formation and stabilisation in the rumen will inhibit eructation and animals will become tympanic. The condition, if severe, will lead to death of cattle.

Ketosis: The dissolved carbon dioxide ($dCO_2$) holdup in the rumen will generate satiety signals that will limit feed intake, the reduction in nutrients intake will trigger fat mobilisation and ketone body production, condition known as ketosis.

Low fat syndrome: The decline in acetic acid in favour of propionic acid production in the rumen will trigger the decline in fat content of the milk. High dissolved carbon dioxide ($dCO_2$) concentrations in the rumen, on one hand stimulate the growth of bacteria that produce large amount of propionic acid. On the other hand acetogenic bacteria will favour other metabolic pathways reducing acetic acid production.

The apparatus, particular a wireless nutrition device can monitor the concentration and evolution of dissolved carbon dioxide ($dCO_2$) in the rumen. The knowledge of threshold associated to the presentations of these diseases will allow farmers, nutritionist and consultants to design diets that promote better rumen fermentation and reduce the prevalence of nutritional diseases on farm.

The invention, especially the inventive sensing unit as a rumen bolus will also help nutritionist and farmers to directly monitor rumen fermentation and will give a first account on feed quality, feeding management and animal performance by optimising rumen bacterial growth. Farmers will be able to feed diets that provide the right balance of nutrient and feeding ruminant at the right time during the day to optimise feed conversion efficiency and milk production.

Fermentation monitoring with the $CO_2$ sensor is achieved by measuring the changes and evolution dissolved carbon dioxide (dCO2) concentration in the rumen liquor. Fermentation is intrinsically related to bacterial growth in the rumen and bacterial growth follows a known cycle:

The lag phase, early in the development and before cell division;

The exponential or logarithmic growth phase, a constant rate of bacterial growth;

The stationary phase, when the exhaustion of nutrients in the media forces bacterial growth to cease, and number of viable bacteria decrease, and.

The decline cell phase (death phase), the number of viable bacteria decline quickly if more nutrients are not supplied, which make the next bacterial growth cycle less efficient.

Carbon dioxide evolution rate (CER) is one important parameter to monitor fermentation. But CER cannot be measured directly on chemostat (in vitro culture) due to the technical difficulties to obtaining dissolved carbon dioxide ($dCO_2$) measurements. Indirect methods had been developed to measure CER, for instance, the carbon transfer rate (CTR), which monitors $CO_2$ release on the outlet of the chemostat. But CTR measurements are not reliable and can be affected by different environmental condition within the broth (such as pH and viscosity). Changes in these factors mean that normally dissolved carbon dioxide ($dCO_2$) concentrations can be 33 to 40% higher than the $CO_2$ concentrations evolving from the broth. For the same reason, mathematical models and algorithms had been developed to compensate for the disturbance in in-vitro conditions and made CTR equivalent to CER. However, CTR monitoring is not applicable for monitoring environmental conditions in the rumen, because of two reasons: first, a large proportion of the exhale $CO_2$ in ruminant comes from respiration, and second, the environmental conditions in the rumen (i.e. peristaltic movements, eructation, rumination, digesta outflow and epithelial absorptive mechanisms, for naming a few factors).

The direct dissolved carbon dioxide ($dCO_2$) measurement in the rumen as proposed in the invention overcomes all these problems. The dissolved carbon dioxide ($dCO_2$) sensor is placed inside the rumen liquor which gives a direct estimation of dissolved carbon dioxide ($dCO_2$) concentrations and evolution. Hence, dissolved carbon dioxide ($dCO_2$), CER and other parameters to monitor bacterial growth cycle can be determined. Therefore, postprandial changes and evolution of dissolved carbon dioxide ($dCO_2$) concentrations might follow bacterial growth and monitoring dissolved carbon dioxide ($dCO_2$) concentrations with an indwelling rumen bolus can provide an accurate measurement of bacterial fermentation.

The real-time monitoring of bacterial fermentation provides an opportunity to influence, particularly to optimise bacterial growth, for instance by reducing the time between lag phase and exponential growth, or by identifying when stationary growth phase begins, and/or by avoiding that rumen fermentation reaches decline phase of growth. In other words, the synchronisation of growth cycles will improve the utilization of nutrient and overall production of by-products. Ultimately, most of the by-products of rumen bacterial growth are used as a source of energy for milk production; similarly most of the protein in milk of dairy cattle comes from the digestion of rumen bacterial cells. Therefore, optimal rumen bacteria growth will mean also optimal energy and protein availability for milk production.

The identification and automatic warnings of different phases of bacterial growth in the rumen can be used by farmers, nutritionist and consultants to improve feeding management routines. For instance, the addition of feed (feeding) at these identifying times within the day might provide rumen bacteria with fresh nutrients and reduce the time between lag phase and following exponential growth, enhancing bacterial growth, and the amount of nutrient available for digestion and absorption. Therefore, adjusting feeding management practices e.g. feeding time will improves nutrient output by synchronising and enhancing bacterial growth. The synchronisation of nutrient supply with bacterial growth in the rumen also has been shown to improve feed intake, feed conversion efficiency, and milk production in dairy cattle.

Another relevant application could be the use of warning signals due to changes in bacterial growth to activate automatic feeding equipment (feeder and push-ups robots) to deliver feed to a specific animal, feeding group or herd. This can be achieved by transmitting the information obtained from the rumen of animals or group of cows equipped with the system, in real-time, to a central processing system that will control and activate the equipment to deliver feed. For that, the system will be designed to transmit the information, while the animal is being milked or emitting the information to receivers conveniently allocated around the barn, i.e. in the feeding area.

On the other hand, by analysing dissolved carbon dioxide ($dCO_2$) data transmitted wirelessly from single individual animal, feeding group or herd, the best daily routine of feeding for that particular individual or set of animals can be established. The feeding routine can be adjusted, after a few hours of data processing, if changes in diet or component occurs, such as the opening of new batches of silage or the addition of new feed components. With this information an optimal feed intake can be obtained and higher milk production with lower nutritional problems might be achieved.

Monitoring bacterial growth and fermentation using dissolved carbon dioxide ($dCO_2$) sensors becomes more important if we think of monitoring feed quality and feed composition. The evaluation of feed digestibility for ruminants can be easily monitored using in vitro gas production systems; they provide an idea of the amount of fermentative material present in the different components of a ruminant diet. Those systems are based on measuring the release of gas from the incubation of nutrient in a sealed container which mimics the in vivo fermentation in the rumen; $CO_2$ is the main gas collected using this methodology. Daily cattle diets also are set according to the nutrient content of the different components (evaluated separately); however the quality and quantity of nutrients of those components are highly variable on farm. Therefore, the mixing and a particular diet (with several components) do not warrant the provision of appropriated amount of nutrients for an adequate fermentation and milk production. This whole problem of quantity and quality of the diet is complicated by the cattle's habits of feed selection while feeding.

Indwelling dissolved carbon dioxide ($dCO_2$) rumen bolus and real-time monitoring of dissolved carbon dioxide ($dCO_2$) evolution can be used as live monitoring of the digestibility of ruminant diets in a similar way as the in vitro system. The analysis of individual, feeding group and herd information will provide direct insight on the fermentative quality of the feed given to those animals. Because the feed information comes from the true intake of cattle, the information will reflect better the true nutritional value of the ration provided to each individual cow and also the whole herd.

For instance, a decline in the rumen exponential growth phase might indicate that specific diets lack of some of the nutrient required for optimal bacterial growth or if the stationary phase is reached faster with another diet, it might suggest that that particular diet is rich in highly fermentative material, but might lack of the right amount of fiber for an adequate rumen fermentation. This information can be directly correlated to the milk yield for a single animal or group of cows (i.e. feeding group) and a clear idea of the nutrition value of a specific diet for feeding cattle can be achieved.

In other words, the information collected from a large set of animals within the herd will help to evaluate the nutritional value of the feed given in that specific herd or feeding group. Algorithms can be created to generate realtime warnings of the decline on feed quality or the lack nutrients that might limit optimal rumen fermentation (i.e. fiber content of the diet) and milk production. Therefore, farmers, nutritionist and consultants will be able to quickly modify quantities and components to optimise rumen bacterial growth, increase milk production and reduce nutritional diseases. As above, the integration with automatic feeding systems will enable the optimization of diets in a day by day basis, enhancing milk production and reducing nutritional diseases on farm.

Changes and saturation of rumen liquor with dissolved carbon dioxide ($dCO_2$) can limit or change bacterial growth, bacterial metabolism and by-products of biochemical reactions of bacteria. The real-time monitoring of dissolved carbon dioxide ($dCO_2$) concentrations will enable farmers to identify when different threshold are reached and different biochemical pathways might be activated, which might alter the end-products of those reactions. In a similar way, high dissolved carbon dioxide ($dCO_2$) concentrations might shift bacteria populations in the rumen to groups that are better adapted to those environmental conditions; those bacteria might produce different end-products which in turn might change the overall concentrations of nutrient in the rumen.

As an example and depending on other environmental conditions (mainly temperature) the following threshold can be found in the rumen. Optimal bacterial growth required dissolved carbon dioxide ($dCO_2$) concentrations between ~12 mM and ~20 mM, on those conditions the main product of fermentation is acetic acid, higher concentrations (greater than 20 mM) might enhance propionic acid concentrations (~60 mM is optimal for large production of propionic acid in batch systems) and the increase in lactic acid production (~120 mM) might be seen due to excessive dissolved carbon dioxide ($dCO_2$) accumulation.

A monitoring of dissolved carbon dioxide ($dCO_2$) concentration in the rumen liquor will help farmers, nutritionist and consultants, not only to identify risk health factors such as excessive accumulation of lactic acid and propionic acid, but also to optimise propionic acid (main energy source for cattle and for milk protein production) and acetic acid production (milk fat production) to provide optimal milk quality (optimal milk protein/fat ratio). With this tool farmers, nutritionist and consultants might be able to design diets that promote better rumen fermentation for optimal milk quality production and might reduce risk factors associated to nutritional diseases. Algorithms will be designed to monitor in real-time dissolved carbon dioxide ($dCO_2$) concentration providing a relationship between short chain fatty acid concentrations (propionic, acetic, butyric and lactic acid) and thresholds will be established to correlate these important nutritional factors with milk quality.

Methane ($CH_4$) is a waste product of fermentation and one of the main greenhouse gases in the atmosphere, by monitoring the methane concentrations during fermentation, a good indication of amount of methane being produced by specific animals and/or diet might be obtained. The dissolved $CH_4$ concentrations can be measured directly with a specific NIRS sensor for methane and the evolution of methane during the day will give a good indication of the amount of $CH_4$ produced by a certain animal, group of animals and diets.

The combination of methane sensor information with milk yield data per individual animals, feeding groups or herds will provide nutritionist and farmers with the possibility to adapt diets and minimize methane emissions. By feeding diets that can achieve a reduction in methane production during fermentation, farmers could obtain higher feed conversion efficiency (more milk been produced per kg of feed given), or the selection of animals that digest diets with higher conversion efficiency (producing more nutrients and less methane).

An indirect approach for measuring conversion efficiency and methane emissions is by instead measuring dissolved carbon dioxide ($dCO_2$) concentrations. There is a direct relationship between $CO_2$ and $CH_4$ production in the rumen; Methanogens bacteria produce $CH_4$ by reducing $H_2$ and $CO_2$, this process is optimal at lower dissolved carbon dioxide ($dCO_2$) concentrations (<60 mM) whereas higher dissolved carbon dioxide ($dCO_2$) concentrations will tend to reduce $CH_4$ formation, as other metabolic pathways for energy production might be favored, and/or other bacteria populations better adapted to thrive in high $CO_2$ conditions replace Methanogens. Therefore, cataloguing animals between high and low dissolved carbon dioxide ($dCO_2$) producer might find that animals with higher dissolved carbon dioxide ($dCO_2$) concentrations or daily evolution tend to produce less methane and convert feed more efficiently than low dissolved carbon dioxide ($dCO_2$) emitters.

In a similar way, bacterial populations in the rumen are unique and very stable for each individual animal, herd or group of animals. Establishment and maintenance of a particular bacterial population depends on the diet that animals received, but also on the internal environmental conditions of the rumen, most remarkably dissolved carbon dioxide ($dCO_2$) concentration. Hence, fermentation characteristic measured by monitoring dissolved carbon dioxide ($dCO_2$) concentrations and evolution will indicate which animals are more efficient into maintaining a large biomass of bacteria that are capable to digest nutrients more efficiently (less waste in the form of $CH_4$). The relationship between dissolved carbon dioxide ($dCO_2$) evolution and milk production of the animal might be a direct method to estimate fermentative efficiency and an indirect method to determine high methane emitters.

Algorithms and equations will be created to show, in a clear and consistent way, differences between and within animals, groups and herds. Similarly, methane production can be monitored externally and values correlated to dissolved carbon dioxide ($dCO_2$) concentration and evolution measured directly. By combining CH4 emissions (real or estimated), dissolved carbon dioxide ($dCO_2$) evolution and individual milk information, we can have a close approximation on the feed conversion efficiency and methane emissions. The information can be used by breeders, nutritionist, farmers and consultants to select more efficient animals (higher conversion feed efficiency, less methane ($CH_4$) emissions), similarly the information might be used to select the most efficient diets or nutrients to minimize energy losses and $CH_4$ emissions in a group or herd basis (optimal feed conversion efficiency for milk production).

Although the invention is illustrated and described herein as embodied in a method and apparatus for monitoring nutrition, especially fermentation in a rumen of a ruminant, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE DRAWINGS

Figure 1:
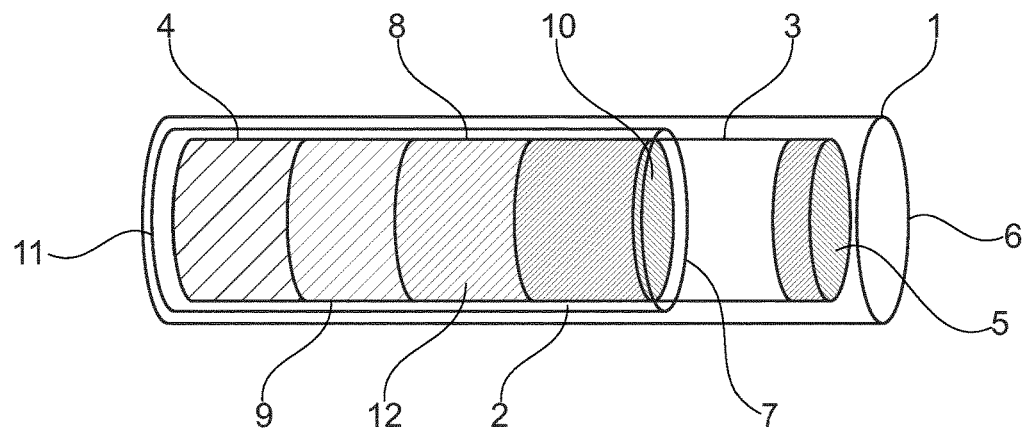
FIG. 1 an example of an apparatus for monitoring nutrition in the rumen of a ruminant.

FIG. 1 displays an example of an apparatus 1 for monitoring nutrition, especially fermentation in a rumen of a ruminant, wherein a characteristic value of dissolved carbon dioxide inside the rumen is determined. This apparatus 1 comprises a sensing unit 2 with a measurement chamber 3. It further comprises a first communication unit 4. The measurement chamber 3 is limited by a reflecting surface 5. Measurement chamber 3 and reflecting surface 5 are encased by a PTFE membrane 6 allowing the diffusion of carbon dioxide dissolved in the rumen liquid surrounding the apparatus 1 into the measurement chamber 3. There, infrared light is emitted from a light emitting diode in the sensing unit 2 through a glass cover 7 into the measurement chamber 3. The light passes the gas in the measurement chamber 3, is reflected by the reflecting surface 5 and is sensed in the sensing unit 2. From the light sensed in the sensing unit 2 the carbon dioxide content in the measurement chamber 3 can be gathered following the usual principles of an NDIR sensor. As an equilibrium is assumed between the gas dissolved in the rumen liquid and in the measurement chamber 3 this allows the monitoring of the concentration of dissolved carbon dioxide in the rumen liquid.

The data gathered can be correlated with a pH value by a correlation means 12 being part of a control unit 8 having a memory for storing data. The control unit 8 can be part of a computing unit and/or can comprise integrated circuits. The method according to the present invention can preferably be performed in or with the control unit 8. The correlated pH value and/or the concentration of dissolved carbon dioxide can be transmitted to a second communication unit (see FIG. 3) via the first communication unit 4. Furthermore, the apparatus 1 comprises a battery 9 for providing electrical energy to the first communication unit 4, the control unit 8 and the sensing unit 2. First communication unit 4, battery 9, control unit 8 and sensing unit 2 are covered by an encasement 11 made from stainless steel to take care of possible corrosion problems.

The sensing unit 2 comprises a temperature sensor 10 as well.

Figure 2:
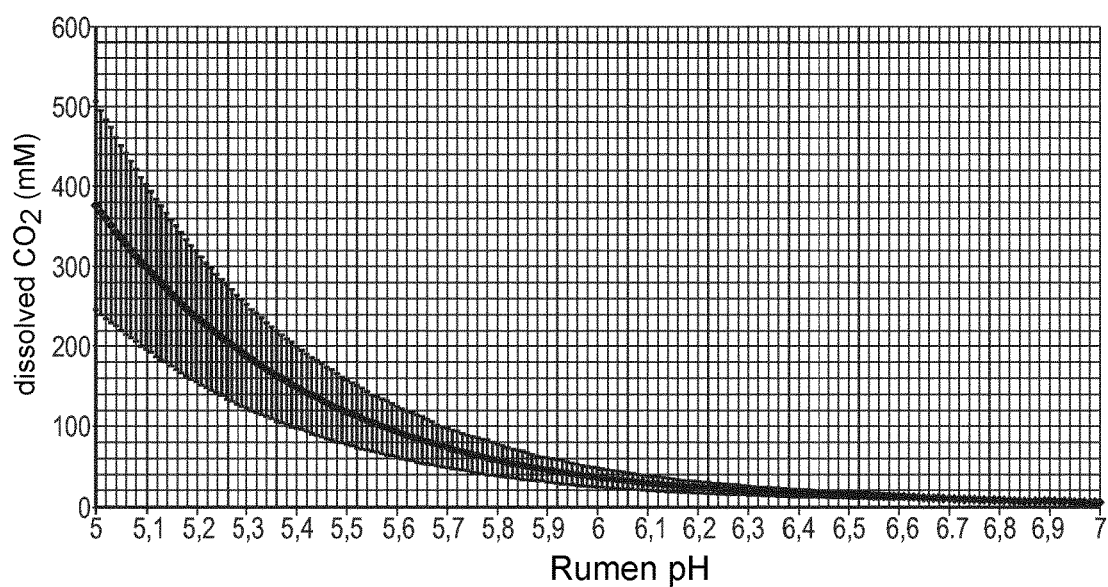
FIG. 2 an example of a correlation between the concentration of dissolved carbon dioxide in the rumen and the respective pH values.

FIG. 2 displays one possible correlation between the measured concentration of dissolved carbon dioxide and the pH value in the rumen liquid. The measurement of a concentration of dissolved carbon dioxide (shown on the y-axis of the diagram) is correlated to a range of pH values (shown on the x-axis of the diagram). This allows correlation of one concentration of dissolved carbon dioxide with a range of pH values. If the effect on the animal, e. g. regarding acidosis, is monitored based on the measurement values it is possible to use the minimum pH value of the interval to allow the correlation with one single pH value which is relevant for the understanding of a possible acidosis to be developed by the animal.

Figure 3:
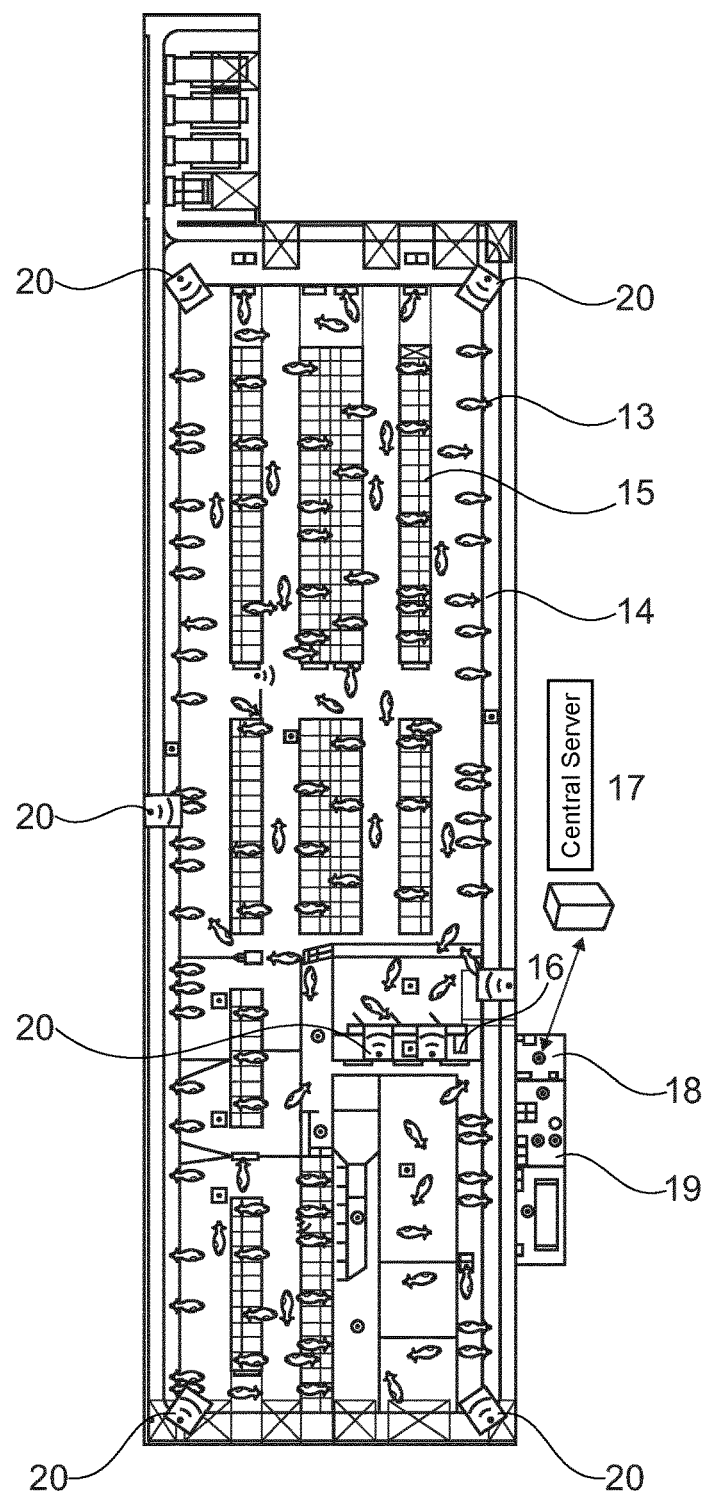
FIG. 3 an example of a milking parlor with a communication unit for to communicate with an apparatus for monitoring the concentration of dissolved carbon dioxide in the rumen of a ruminant.

FIG. 3 shows an example of a milking parlor of a communication unit for to communicate with an apparatus for monitoring the concentration of dissolved carbon dioxide in the rumen liquid of a ruminant. FIG. 3 shows as an example a dairy parlor. The dairy parlor has different zones for the ruminants Ruminants 13 can visit for example the feeding table 14, a lying area 15 or an automatic milking system 16 as examples. Within the dairy parlor there are placed second communication units 20. The second communication units 20 can contact and ask for wireless information to the first communication units which are placed in the rumen of ruminants. The second communication units 20 communicate with a central processing system 18. The central processing system 18 being part of a dairy management system. The data which are transmitted to the central processing system can be processed and analyzed by the central processing system. Via a wireless connection the data received by the central processing system be transmitted for example to a central server 17 or to a farmer's office 19.

The invention claimed is:

1. A method for monitoring nutrition, especially fermentation in a rumen and/or reticulum of a ruminant, the method comprising the steps of:
    directly measuring a concentration of dissolved carbon dioxide from only the liquid inside the rumen and/or reticulum; and
    using the measured concentration of dissolved carbon dioxide to monitor for nutritional syndromes or diseases in the gastro-intestinal track of the ruminant.

2. The method of claim 1, wherein the concentration of dissolved carbon dioxide is correlated with at least one pH value.

3. The method of claim 1, wherein the concentration of dissolved carbon dioxide is directly measured using an infrared sensor.

4. The method of claim 1, wherein the step of directly measuring the concentration of dissolved carbon dioxide is measured at predetermined times.

5. The method of claim 1, and further comprising the step of:
    correlating a directly measured concentration of dissolved carbon dioxide with a respective pH value.

6. The method of claim 5, and further comprising the step of:
    calculating the respective pH value based on a predetermined relationship between a concentration of dissolved carbon dioxide and the respective pH value.

7. The method of claim 1, and further comprising the step of:
    transmitting wirelessly to a receiver outside the ruminant at least one of the following data
    a) a directly measured concentration of dissolved carbon dioxide and/or
    b) a respective pH value.

8. The method of claim 1, and further comprising the step of:
    measuring the temperature in the rumen and/or reticulum.

9. Apparatus for monitoring nutrition, especially fermentation in a rumen and/or reticulum of a ruminant, the apparatus comprising of a ruminant, the apparatus comprising:
    a) a submergible dissolved carbon dioxide sensing unit to directly sense a concentration of dissolved carbon dioxide in only the rumen and/or reticulum liquid;
    b) a wireless communication unit configured to communicate with a respective second communication unit outside the ruminant, wherein the apparatus is shaped to be orally applied to the ruminant and to remain permanently in the rumen and/or reticulum; and
    c) using the directly measured concentration of dissolved carbon dioxide to monitor for nutritional syndromes or diseases in the gastro-intestinal track of the ruminant.

10. The apparatus of claim 9, wherein the dissolved carbon dioxide sensing unit includes an infrared sensor positioned to directly sense a concentration of dissolved carbon dioxide in the rumen and/or reticulum liquid.

11. The apparatus of claim 10, wherein the submergible carbon dioxide sensing unit comprises a light emitting source of a same wavelength emitted by the infrared sensor.

12. The apparatus of claim 9, and further comprising a rumen temperature sensor.

13. The apparatus of claim 9, and further comprising:
    a correlation unit programmed to correlate the concentration of dissolved carbon dioxide with at least one pH value.

14. The apparatus of claim 9, and further comprising an encasement made at least in part from stainless steel and in which the dissolved carbon dioxide sensing unit is at least partially disposed.

15. The apparatus of claim 9, and further comprising:
    a pH sensor disposed in the rumen and/or reticulum.

16. A milking parlor, comprising:
    apparatus for monitoring nutrition, especially fermentation in a rumen and/or a reticulumof a ruminant, the apparatus comprising:

a submergible dissolved carbon dioxide sensing unit to sense a concentration of dissolved carbon dioxide directly from the rumen and/or reticulum liquid;

a first wireless communication unit configured to communicate with a respective second communication unit outside the ruminant, wherein the apparatus is shaped to be orally applied to the ruminant and to remain permanently in the rumen and/or reticulum;

a correlation device programmed to correlate the value of the concentration of dissolved carbon dioxide to monitor for nutritional syndromes or diseases in the gastro-intestinal track of the ruminant; and the second communication unit is disposed in the milking parlor for wireless communication with the first wireless communication unit.

* * * * *